(12) United States Patent
Navarrini et al.

(10) Patent No.: US 6,300,526 B1
(45) Date of Patent: Oct. 9, 2001

(54) HYDRO-FLUOROALKYLVINYLETHERS AND PROCESS FOR OBTAINING THEM

(75) Inventors: Walter Navarrini; Antonio Russo, both of Milan (IT)

(73) Assignee: Austmont S.p.A., Milan (IT)

( * ) Notice: Subject to any disclaimer, the term of this patent is extended or adjusted under 35 U.S.C. 154(b) by 0 days.

(21) Appl. No.: 09/362,706

(22) Filed: Jul. 29, 1999

(30) Foreign Application Priority Data

Jul. 31, 1998 (IT) .............................. MI98A1792

(51) Int. Cl.$^7$ .................. C07C 43/11; C07C 41/09; C08F 259/08; C08F 261/06
(52) U.S. Cl. .................. 568/614; 568/615; 568/616; 568/618; 568/669; 568/683; 568/684; 568/685; 525/276; 525/298; 525/312; 525/314
(58) Field of Search .................. 568/614, 615, 568/616, 618, 669, 683, 684, 685; 525/276, 298, 312, 314

(56) References Cited

U.S. PATENT DOCUMENTS

| | | | |
|---|---|---|---|
| 3,642,742 | 2/1972 | Carlson | 260/87.5 A |
| 3,817,960 | 6/1974 | Resnick | 260/87.5 A |

FOREIGN PATENT DOCUMENTS

| | | | |
|---|---|---|---|
| 0 184459 A2 | 6/1986 | (EP) | C08F/214/26 |
| 0 338755 B1 | 10/1989 | (EP) | C08F/214/26 |
| 812 116 | 4/1959 | (GB) | |
| 96/17877 * | 6/1996 | (WO) | C08F/214/22 |
| 96/41823 | 12/1996 | (WO) | C08F/214/26 |

OTHER PUBLICATIONS

G.S. Misra et al., "Redox Polymerization", *Prog. Polym. Sci.*, vol. 8, pp. 61–131, 1982.

O. Paleta et al., "The Chemo–Selective Reduction of Fluorinated Halogenoesters With Sodium Borodhride–Fluorinated Halogenaolkanols and their (Meth) Acrylates", *Journal of Fluorine Chemistry*, vol. 45, pp. 331–348, 1989.

* cited by examiner

*Primary Examiner*—Rosalynd Keys
(74) *Attorney, Agent, or Firm*—Arent Fox Kintner Plotkin & Kahn PLLC

(57) ABSTRACT

Hydro-2,2-difluoroalkylvinylethers having the formula $$CF_2=CH-O-R_A \qquad (I)$$

wherein $R_A$ is a radical containing fluorine, optionally containing halogens such as Cl, Br, I, hydrogen, functional groups CM, COOR', CON(R')$_2$, SO$_2$OR', m wherein R' is a $C_1$–$C_5$ alkyl, $R_A$ being selected from the following:

a linear or branched, saturated or unsaturated $C_2$–$C_{20}$ fluoroalkyl, or a saturated or unsaturated $C_4$–$C_6$ fluorinated cyclic group wherein optionally from 1 to 2 carbon atoms are substituted with oxygen atoms, or a linear, branched saturated or unsaturated, $C_3$–$C_{15}$ fluorooxyalkyl group, containing one or Core oxygen atoms.

10 Claims, No Drawings

HYDRO-FLUOROALKYLVINYLETHERS AND PROCESS FOR OBTAINING THEM

The present invention relates to fluoroalkylvinylethers showing high reactivity in the polymerization processes with totally or partially fluorinated ethylenically unsaturated monomers.

More specifically the present invention relates to hydro-fluoralkylvinylethers giving TFE polymers thermally more stable than the known hydro-fluoroalkylvinylethers, the hydrogen atoms being equal. Furthermore the fluoroalkyl-vinylethers of the invention are obtainable with high yields by an industrially simpler process in comparison with the known processes since it requires very mild reaction conditions.

It is known that partially or totally fluorinated fluoroalkylvinylethers are used to obtain thermoplastic or elastomeric fluorinated polymers, the commercial importance of which is based on their sole property combination, among which the high thermal and chemical stability.

It is known that some fluoropolymers, such as for example polytetrafluoroethylene, are processable with difficulty since they have a very high melt viscosity. In the art the tetrafluoroethylene (TFE) polymer processability is improved by TFE copolymerization with other ethylenically unsaturated molecules, such as for example (per) fluorovinyl-ethers.

The totally fluorinated vinylethers show low reactivity in the polymerization process. In these processes it is necessary to recover the unreacted vinylether, making the cost of the polymeric manufactured article more expensive.

The synthesis methods used to obtain hydrofluoroalkylvinylethers are unsatisfactory since they require an anhydrous reaction enrvironment, high TFE pressures and high reaction temperatures around 80–100° C.

GB patent 812,116 relates to hydro-fluorovinylethers having the formula $CH_2=CF-O-R^T$, wherein $R^T$ is equal to alkyl or to a fluorinated alkyl, their synthesis and polymerization. These vinylethers have an high reactivity and they easily copolymerize. The process for preparing the described vinylethers is carried out by reacting a $R^T-CH^2-O^-$ alcoholate with TFE giving yields of about 40%, but it requires rather drastic reaction conditions: high anhydricity, high TFE pressures (p>20 atm), high reaction temperatures in the range 85°–90° C.

EP patent 338,755 relates to a process for preparing perfluorinated copolymers comprising from 99.5% to 50% by moles of TFE and from 0.5% to 50% by moles of an hydrovinylether of formula $CF_2=CFOCH_2C_{n'}F_pX'_m$  ($X'=Cl$, Br, n' is an integer comprising zero, p ranges from 0 to (2n'+1); m=0,1; p+m≦1n'+1). The copolymers obtained by reaction of the two monomers are fluorinated with elemental fluorine, obtaining more stable polymers. In the copolymers formed by TFE and $CF_2=CF-O-CH_2-CF_2-CF_3$ the thermal degradation temperature of the non fluorinated polymer is 380° C. when the fluorovinylether molar percentage is 5.8% and it is 330° C. when the molar percentage is 25%. The thermal decomposition temperatures of the corresponding fluorinated polymers are higher than 60° C. and 80° C. respectively. This patent shows that the thermal stability of these copolymers depends on the vinylether amount and that the stability decreases as the molar percentage increases.

In the patent application WO 96/41823 elastomeric polymers obtained by TFE copolymerization with hydro-vinylethers of formula $CF_2=CF-O-R_B$ wherein $R_B$ is a $C_1-C_6$ alkyl group, are described. The thermal stability of the corresponding polymers with TFE is similar to that of the non fluorinated copolymers of EP 338,755.

The need was felt to have available hydro-fluorovinylethers ethers allowing to obtain polymers having an improved thermal stability.

The need was felt to have available a simpler process using milder reaction conditions and with high yields with respect to those of the prior art to obtain hydrofluorovinylethers.

It has now been surprisingly and unexpectedly found that it is possible to meet said requirements with new hydrofluorovinylethers giving TFE polymers with an improved thermal stability in comparison with the hydrofluorovinylethers of the prior art (see for example EP 338, 755 and Table 1).

It is an object of the present invention hydro-2,2-difluoroalkylvinylethers having the formula $$CF_2=CH-O-R_A \qquad (I)$$

wherein $R_A$ is an alkyl radical containing fluorine, optionally containing halogens such as Cl, Br, I; hydrogen, and $R_A$ is selected from the following:

linear or branched, saturated or unsaturated $C_2-C_{20}$ fluoroalkyl group;

saturated or unsaturated $C_4-C_6$ fluorinated cyclic group; wherein optionally from 1 to 2 carbon atoms can be substituted with oxygen atoms forming ether bonds;

linear, branched saturated or unsaturated $C_3-C_{15}$ fluorooxyalkylic group, containing one or more oxygen atoms forming ether bonds.

Preferably the $R_A$ radical has the following meanings:
$CF_2-R_C$ 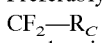
wherein $R_C$ is selected from the following:
a linear or branched, saturated or unsaturated $C_1-C_{19}$ fluoroalkyl group;
a linear or branched, saturated or unsaturated $C_2-C_{14}$ fluorooxyalkyl group, containing one or more oxygen atoms forming ethereal bonds;

$CF_2-CFH-R_D$ 
wherein $R_D$ is selected from the following:
a linear or branched, saturated or unsaturated $C_1-C_{18}$ perfluoroalkyl group;
a linear or branched, saturated or unsaturated $C_1-C_{13}$ perfluorooxyalkyl group, containing one or more oxygen atoms forming ether bonds.

$R_A$ optionally contains stable functional groups in the reaction conditions for the preparation of vinylether (I), for example, CN, COOR', CON(R')$_2$, SO$_2$OR', wherein R' is a linear or branched $C_1-C_5$ alkyl.

The hydro-fluoroalkylvinylethers of the invention allow to obtain, the percentage by weight of the contained hydrogen being equal, polymers having an higher thermal stability than that of the polymers of the hydro-fluoroalkylvinylethers of the prior art. See Table 1 for the TFE polymers.

The hydro-fluoroalkylvinylethers of the invention show in the polymerization an higher reactivity than the perfluorovinylethers of the art. See the Examples.

Polymers and copolymers can be obtained by copolymerizing with the hydro-fluoroalkylvinylethers of the present invention totally or partially fluorinated and non fluorinated comonomers having at least an unsaturation of ethylenic type.

Among the usable comonomers the following ones can be mentioned:

$C_2-C_8$ perfluoroolefins, such as tetrafluoroethylene (TFE), hexafluoropropene (HFP), hexafluoroisobutene;

hydrogenated $C_2$–$C_8$ fluoroolefins, such as vinyl fluoride (VF) trifluoroethylene, perfluoroalkylethylene $CH_2=CH-R_f$, wherein $R_f$ is a $C_1$–$C_6$ perfluoroalkyl;

chloro- and/or bromo- and/or iodo-$C_2$–$C_8$ fluoroolefins, such as bromotrifluoroethylene;

(per)fluoroalkylvinylethers (PAVE) $CH_2=CFOR_f$, wherein $R_f$ is a $C_1$–$C_6$ (per)fluoroalkyl, such as trifluoromethyl, bro-modifluoromethyl or heptafluoro-propyl;

$CF_2=CFOX"$ (per)fluoro-oxyalkylvinylethers, wherein $X"$ is: a $C_1$–$C_{12}$ alkyl, or a $C_1$–$C_{12}$ oxyalkyl, or a $C_1$–$C_{12}$ (per)fluorooxyalkyl having one or more ether groups, for example perfluoro-2-propoxy-propyl;

perfluorodioxole (PD), perfluoro (2,2-dimethyl)-1,3-dioxole (PDD), perfluoro-4-methoxy-1,3-dioxole (TTD);

$CF_2=CF-O-CF_2-O-CF=CF_2$ (bis-vinyloxymethane, BVOM);

$CF_2=CF-O-CF_2-CF_{2-SO_2}F$.

Optional comonomers which can be copolymerized are non fluorinated $C_2$–$C_6$ olefins, such as ethylene, propylene, isobutylene.

The copolymerization products can be prepared by radical polymerizations, both in aqueous and organic medium.

In the polymerizations in aqueous medium, the polymerization initiator can be any substance able to produce radicals, such as for example peroxides, persulphates or azo-compounds. Optionally also a reducing agent can be used, such as for example an iron salt, in order to favour the initiator decomposition. Optionally, a chain transfer agent is used to obtain the desired molecular weight. The polymerization in aqueous environment requires the presence of an emulsifying agent. See for example EP 184,459.

Alternatively, polymerizations can be carried out in organic solvent as described for example in U.S. Pat. No. 3,642,742. Any initiator suitable for the TFE polymerization in organic solvent can be used. Examples of initiators are alkylpercarbonates, perfluoroacylperoxides, benzoyl peroxide and azo-bis-(isobutyronitrile).

Redox systems can also be used. See *Prog. Polym. Sci*, 8, 61 (1982). The solvent is generally selected from hydrofluorocarbons, hydrochlorofluorocarbons and perfluoropoly-ethers, optionally containing one or more hydrogen atoms in the terminals.

The hydro-fluoroalkylvinylethers of the invention, as said, are usable for obtaining thermoplastic and elastomeric fluorinated polymers used for applications well known in the art but, that in comparison with the corresponding polymers using the hydro-fluoroalkylvinylethers of the art, the hydrogen atoms being equal, show higher thermal stability.

A further object of the present invention is a process for obtaining the new hydro-fluoroalkylvinylethers, wherein one of the starting reactants is a 2-Hal-2,2-difluoroethyl alcohol, wherein Hal=Cl, Br, preferably Cl, obtainable by methods of the art for example as described by 0. Paleta, J. Fluorine Chem., 45, 331–348 (1989), said process comprising the following steps:

A) preparation of a 2-Hal-2,2-difluoroethyl fluoroalkyl ether by reaction of the 2-Hal-2,2-difluoroethyl alcohol in the presence of an alkaline or earth-alkaline metal hydroxide, in molar ratio with respect to the alcohol in the range 0.2–1, with an unsaturated compound selected from the following:

A1) an unsaturated fluoroalkyl compound having the formula

XFC=CYZ (II)

according to the following reaction scheme:

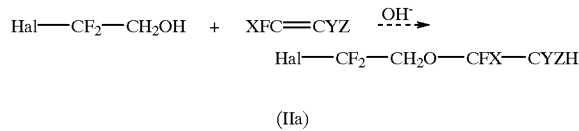

(IIa)

wherein:
the total number of carbon atoms of —CFX—CYZH is as defined for $R_A$;
X=F, $R'f_X$, $OR'f_X$, preferably F;
Y=F, H, Cl, Br, I, $R'f_Y$, $OR'f_Y$;
Z=F, H, Cl, Br, I, $R'f_Z$, $OR'f_Z$;
when one or more fluorooxyalkylic groups are present the total number of oxygen atoms must be equal to that of $R_A$'S;
$R'f_X$, $R'f_Y$, $R'f_Z$, equal to or different from each other, are fluorinated alkylic groups which optionally contain one or more oxygen atoms forming ethereal bonds and/or one or more halogen atoms such as Cl, Br, I; $R'f_X$, $R'f_Y$, $R'f_Z$ optionally contain also one or more functional groups such as CN, COOR', CON(R')$_2$ wherein R' is as above defined;

A2) A perfluorinated $C_4$–$C_6$ cyclic compound containing a double bond, in which optionally from 1 to 2 carbon atoms can be substituted with oxygen atoms (compound III); when no oxygen is directly bound to the unsaturation, the reaction scheme is the following:

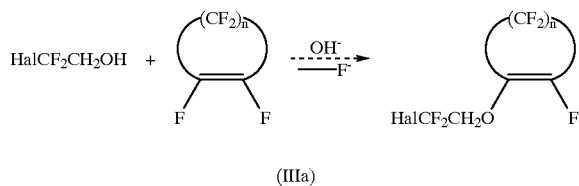

(IIIa)

wherein n is an integer comprised between 2 and 4;
otherwise the reaction runs as in A1) and a saturated compound is obtained;

A3) a disubstituted perfluoroalkyne having the formula:

according to the following scheme:

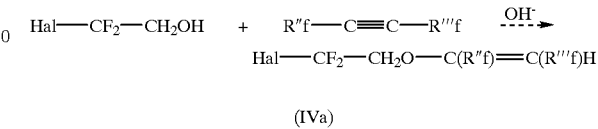

(IVa)

wherein:
R"R"f and R"'f are F or $C_1$–$C_2$ perfluoroalkyl, preferably $C_1$, with the proviso that R"f and R"'f are not contemporaneously F;
the solvent is an organic solvent, suitable for nucleophilic attack reactions and the temperature is in the range 0° C.–50° C;
the reaction mixture is then diluted with slightly acid water, the organic phase is separated and the reaction product is recovered;

B) fluoroalkylvinylether obtainment by dehydrohalogenation of the fluoroalkyl Hal-difluoroethylethers obtained in the preceding step, in the presence of organic or inorganic bases, in aqueous or organic solvent or mixtures thereof, and recovery of the final product according to the methods known in the art.

In step A) the organic solvent can be polar or unpolar, preferably polar, and it is for example ethylic ether, dioxane, dimethylsulphoxide, dimethylformamide, diglyme, tert-butylic alcohol, acetone, methylen chloride; hydroxide is preferably of an alkaline metal, preferably KOH or NaOH; the temperature is in the range 10° C.–40° C. and the reaction is carried out at a pressure which depends on the olefin or the used alkyne, and it can range between 1 and 10 atm.

In step B) dehydrohalogenation is preferably carried out under phase transfer conditions, by using as phase transfer agent a phosphonium salt or a quaternary ammonium salt; preferably the alkali is aqueous and has a concentration in the range 20%–60% w/w, preferably 30%–50% w/w and the alkali is KOH, NaOH or $K_2CO_3$; the temperature is in the range 20° C.–100° C., preferably 30° C.–80° C.

At the end the mixture is diluted with slightly acid water, the organic phase is separated and the reaction product is recovered.

The products which are isolated generally have a purity higher than 90%. The purity degree can be increased with known processes (for ex. distillation).

The invention process can be further simplified and it is possible to obtain by a single reaction the hydro-fluoro-alkylvinylethers of the present invention by reacting, at a temperature in the range 50° C.–80° C. the 2-Hal-2,2-difluoro-ethyl alcohol, wherein Hal is as above defined, with one of the unsaturated compounds (II), (III), (IV) (as defined in step A)), using as solvent tert-butyl alcohol, in the presence of an alkaline or earth-alkaline metal hydroxide in such amount that the molar ratio with the 2-Hal-2,2-difluoroethyl alcohol is in the range 2–5; at the end it is diluted with slightly acid water, the organic phase is separated and the reaction product is recovered. The hydroxide is preferably KOH.

In the invention process the pressure is depending on the olefin, or the used alkyne, and it is in the range 1–10 atm.

A further advantage of the processes according to the present invention resides in the fact that waste materials are aqueous solutions of inorganic salts such as for example KCl or NaCl and can be easily disposed.

The following examples have the purpose to illustrate the invention and they are not to be intended as limitative of the scope of the same.

EXAMPLE 1

Perfluoro-2,5-dihydro-3-oxa-1-pentene $CF_2$=$CHOCF_2CF_2H$ preparation

Example 1A

Perfluoro-1-chloro-2,2,5-trihydro-3-oxa-pentane $ClCF_2$—$CH_2$—$O$—$CF_2CF_2H$ preparation In a 370 ml volume steel reactor equipped with magnetic stirring 22.3 g (0.19 moles) of $ClCF_2$—$CH_2$—$OH$, 45 ml of tert-butyl alcohol and 10.6 g (0.19 moles) of KOH, are introduced. The autoclave is then cooled at −196° C. with liquid nitrogen, evacuated and then charged by condensing 24.2 g (0.24 moles) of TFE. The reaction mixture is slowly let to heat up to room temperature and then kept at this temperature for 8 hours, maintaining stirring in the reaction mixture. During this time the reactor internal pressure decreases from 10 atm to 2 atm.

The TFE in excess is removed from the reactor and the organic phase is diluted with water, then collected and washed two times with slightly acid water by HCl and then anhydrified. 30 g of product showing 73% yield are obtained.

Perfluoro-1-chloro-2,2,5-trihydro-3-oxa-pentane characterization

Boiling point: 83° C.

$^{19}$FNMR in ppm referred to $CFCl_3$=0; −63.1 (2F, —$ClCF_2$); −92 (2F, —$OCF_2$—); −137.1 (2F, —$CF_2H$).

$^1$HNMR in ppm referred to TMS=0: 4.33 (2H, $CH_2$); 5.8 (1H, $CF_2H$).

Mass spectrum (EI), main peaks and attributions: 181 ($M^+$-Cl); 131 ($C_3F_4H_3O^+$) ; 101 ($C_2F_4H^+$, 100%); 51 ($CF_2H^+$).

IR, main bands ($cm^{-1}$): 2980, 1283, 1198, 1132, 975, 931, 775.

Example 1B

Obtainment of perfluoro-2,5-dihydro-3-oxa-1-pentene $CF_2$=$CHOC$—$F_2CF_2H$

In a 50 ml three-necked glass flask, equipped with magnetic stirrer, thermometer, dropping funnel and cold trap (liquid $N_2$), directly connected to the flask by a retort, 3.9 g (0.018 moles) of $ClCF_2$—$CH_2$—$O$—$CF_2CF_2H$ and 1.5 g (0.0009 moles) of tetrabutylammonium hydroxide, are introduced. The reaction mixture is heated up to 70° C. and under strong stirring 2.5 ml of a 50% KOH aqueous solution (equivalent to 1.9 g–0.034 moles of KOH), are added drop by drop. It is allowed to react for 30 minutes and the pressure is lowered to 100 mm Hg. In the cold trap 2.61 g of product are thus collected. The product yield obtained by dehydrochlorination, defined as ratio between the product moles and the $ClCF_2$—$CH_3$—$O$—$CF_2CF_2H$ moles is equal to 80.5%. The reaction conversion was of 81% with a 99% selectivity.

Perfluoro-2,5-dihydro-3-oxa-1-pentene characterization

Boiling point: 39.7° C.

$^{19}$FNMR in ppm referred to $CFCl_3$=0; −137.4 (2F, —$CF_2H$); −110.4 (1F, C=CF); −96.6 (1F, C=CF); −92.3 (2F, —$OCF_2$—);

$^1$HNMR in ppm referred to TMS=0: 5.82 (1H, $CF_2H$); 6.7 (1H, C=CH).

Mass spectrum (EI), main peaks and attributions: 180 ($M^+$); 129 ($M^+$-$CF_2H$); 101 ($C_2F_4H^+$, 100%); 51 ($CF_2H^+$); 29 ($CHO^+$).

IR, main bands ($cm^{-1}$): 2980, 2869, 1779, 1368, 1293, 1262, 1208, 1150, 939, 750.

EXAMPLE 2

Perfluoro-5-bromo-2,5-dihydro-3-oxa-1-pentene $CF_2$=$CH$—$O$—$CF_2CFH$—$Br$ preparation Example 2A Perfluoro-1-bromo-5-chloro-1,4,4-trihydro-3-oxa-pentane $ClCF_2$—$CH_2$—$O$—$CF_2CFHBr$ preparation In a 50 ml glass reactor equipped with PTFE valve and magnetic stirring, 2.4 g (0.02 moles) of $ClCF_2$—$CH_2$—$OH$, 5 ml of tert-butyl alcohol, 1.1 g (0.02 moli) of KOH and 3.5 g of $CF_2$=CFBr (0.022 moles) are fed. The reaction mixture is left under stirring at room temperature for three hours. The organic phase is then diluted with water, separated, washed twice with slightly acid water by HCl and anhydrified. 5 g of a mixture having the following composition: 89% $ClCF_2$—$CH_2$—O—$CF_2CFHBr$ and 11% $CF_2$=CH—O—$CF_2CFHBr$ are obtained.

Perfluoro-1-bromo-5-chloro-1,4,4-trihydro-3-oxa-pentane characterization

Boiling point: 58° C. (150 mm Hg)

$^{19}$FNMR in ppm referred to $CFCl_3$=0; −63.2 (2F, —$ClCF_2$); −86.4 (2F, —$OCF_2$—); −158.4 (1F, —CFHBr).

$^1$HNMR in ppm referred to TMS=0: 4.4 (2H, $CH_2$); 6.4 (1H, CFHBr).

Mass spectrum (EI), main peaks and attributions: 278 (M$^+$); 241 (M-Cl$^+$); 193 ($C_3H_3F_3OBr^+$); 165 ($C_3H_3F_4OCl^+$); 99 ($C_2H_2F_2Cl^+$, 100%).

IR, main bands (cm$^{-1}$): 2976, 2874, 1455, 1409, 1363, 1277, 1229, 1082, 974, 746, 559.

Example 2B

Perfluoro-5-bromo-2,5-dihydro-3-oxa-1-pentene $CF_2$=CH—O—$CF_2CFHBr$ obtainment In a glass flask, equipped as described in the preceding Example 1b, 4 g (0.014 moles) of $ClCF_2$—$CH_2$—O—$CF_2CFHBr$ and 1.5 g (0.0009 moles) of tetrabutylammonium hydroxide are charged. The reaction mixture is heated to 70° C. and under vigorous stirring 1.6 ml of a 50% by weight KOH aqueous solution (equivalent to 1.22 g–0.022 moles of KOH) are added drop by drop and the reaction is allowed to react for 30 minutes. At the end the internal pressure is reduced to 100 mm Hg, collecting in the cold trap 3.42 g of a mixture having the following composition: 70% $CF_2$=CH—O—$CF_2CFHBr$, 30% $ClCF_2$—$CH_2$—O—$CF_2CFHBr$. The dehydrochlorination product yield is 68.8% and the reaction conversion 74.3% with a selectivity equivalent to 92,5%.

Perfluoro-5-bromo-2,5-dihydro-3-oxa-1-pentene characterization $^{19}$FNMR in ppm referred to $CFCl_3$=0; −86.7 (2F, $CF_2O$); −92.7 (1F, C=CF); −110.6 (1F, C=CF); −158.4 (1F, —CFHBr).

$^1$HNMR in ppm referred to TMS=0: 6.1 (1H, C=CH); 6.4 (1H, CFHBr).

Mass spectrum (EI), main peaks and attributions: 240 (M$^+$); 163 ($C_2H_2F_3Br^+$, 100%); 111 (CFHBr$^+$); 80 (Br$^+$).

IR, main bands (cm$^{-1}$): 3149, 3099, 2978, 1774, 1364, 1279, 1174, 1086.

EXAMPLE 3

Perfluoro-2-chloro-1,1-dihydroethyl-1-cyclopentenyl ether preparation

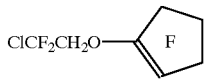

0.8 g (0.007 moles) of $ClCF_2$—$CH_2$—OH are allowed to react with 3 ml of tert-butyl alcohol, 0.4 g (0.007 moles) of KOH and 2.2 g (0.007 moles) of perfluorocyclopentene under the conditions described in the preceding Example 2. 1.7 g of product have been obtained. Yield: 80%.

Perfluoro-2-chloro-1,1-dihydroethyl-1-cyclopentenyl ether characterization $^{19}$FNMR in ppm referred to $CFCl_3$=0; −64.2 (2F, $ClCF_2$); −116.3 (4F, C=C—$CF_2$); −130.2 (2F, $CF_2$); −157.2 ( 1F, C=CF).

1HNMR in ppm referred to TMS=0: 4.7 (2H, $CH_2$)

Mass spectrum (EI), main peaks and attributions: 308 (M$^+$); 273 (M-Cl$^+$); 223 (M-$CF_2Cl^+$); 193 ($C_5F_7^+$, 100%); 143 ($C_4F_5^+$); 99 ($C_2H_2F_2Cl^+$)

IR, main bands (cm$^{-1}$): 2973, 2894, 1733, 1456, 1426, 1396, 1356, 1284, 1208, 1156, 984, 792, 697, 609.

EXAMPLE 4

Perfluoro-2,5-dihydro-3,6-dioxa-1-heptene $CF_2$=CH—O—$CF_2CFHOCF_3$ preparation Example 4A Perfluoro-1-chloro-2,2,5-trihydro-3,6-dioxa-heptane$ClCF_2$—$CH_2$—O—$CF_2CFHOCF_3$ preparation 2.4 g (0.02 moles) of $ClCF_2$—$CH_2$—OH are allowed to react with 5 ml of tert-butyl alcohol, 1.1 g (0.02 moles) of KOH and 3.7 g (0.023 moles) of perfluoromethylvinyl ether under the conditions described in the preceding Example 2. 5.3 g of a mixture 86% of $ClCF_2$—$CH_2$—O—$CF_2CFHOCF_3$ and 14% of $CF_2$=CH—O—$CF_2CFHOCF_3$ were obtained. Perfluoro-1-chloro-2,2,5-trihydro-3,6-dioxa-heptane characterization $^{19}$FNMR in ppm referred to $CFCl_3$=0; −60.7 (3F, $CF_3O$); −63.6 (2F, —$ClCF_2$); −90.4 (2F, —$OCF_2$—) −145.8 (1F, —OCFH).

$^1$HNMR in ppm referred to TMS=0: 4.4 (2H, $CH_2$); 6.4 (1H, OCFH).

Mass spectrum (EI), main peaks and attributions: 197 (M-$CF_2Cl^+$); 181 ($C_4H_3F_6O^+$); 99 ($C_2H_2F_2Cl^+$, 100%).

IR, main bands (cm$^{-1}$): 2979, 1291, 1202, 1128, 977, 678.

Example 4B

Obtainment of perfluoro-2,5-dihydro-3,6-dioxa-1-heptene $CF_2$=CH—O—$CF_2CFHOCF_3$ In a glass flask, equipped as described in the preceding Example 1b, 4.35 g (0.0154 moles) of $ClCF_2$—$CH_2$—O—$CF_2CFHOCF_3$ and 1.5 g (0.0009 moles) of tetrabutylammonium hydroxide, are fed. The temperature is brought to 70° C. and under vigorous stirring 1.7 ml of a 50% KOH aqueous solution (equivalent to 1.3 g–0.023 moles) are added drop by drop. It is allowed to react for 30 minutes. At the end the system pressure is lowered to 100 mm Hg. 3.47 g (0.014 moles) of product are collected in the cold trap. The yield, defined as ratio between the product moles and the $ClCF_2$—$CH_2$—O—$CF_2CFHOCF_3$ moles is of 91.6%.

Perfluoro-2,5-dihydro-3,6-dioxa-1-heptene characterization $^{19}$FNMR in ppm referred to $CFCl_3$=0; −60.7 (3F, $CF_3O$); −90.7 (2F, —$OCF_2$—); −92.8 (1F, —C=CF) −110.6 (1F, C=CF); −145.9 (1F, —CFH).

$^1$HNMR in ppm referred to TMS=0: 6.4 (1H, OCFH); 6.08 (1H, C=CH).

Mass spectrum (EI), main peaks and attributions: 246 (M$^+$); 129 (C$_3$HF$_4$O$^+$); 69 (CF$_3^+$).

IR, main bands (cm$^{-1}$): 2979, 1773, 1291, 1202, 1128, 977, 932, 788, 678.

EXAMPLE 5 perfluoro-2,5-dihydro-3,6,9-trioxa-1-decene
CF$_2$=CH—O—CF$_2$CFHOCF$_2$CF$_2$OCF$_3$ preparation

Example 5A

Perfluoro-1-chloro-2,2,5-trihydro-3,6,9-trioxa-decane ClCF$_2$—CH$_2$—O—CF$_2$CFHOCHCF$_2$CF$_2$OCF$_3$ preparation 2.4 g (0.02 moles) of ClCF$_2$—CH$_2$—OH are allowed to react with 5 ml of tert-butyl alcohol, 1.6 g (0.028 moles) of KOH and 6.2 g (0.022 moles) of perfluoro-3,6-dioxa-1-heptene CF$_2$=CFOCF$_2$CF$_2$OCF$_3$ under the conditions described in the preceding Example 2. 7.1 g of a mixture 80% of ClCF$_2$—CH$_2$—O—CF$_2$CFHO—CF$_2$CF$_2$OCF$_3$ and 20% of CF$_2$=CH—O—CF$_2$CFHOCF$_2$CF$_2$OCF$_3$ were obtained.

Perfluoro-1-chloro-2,2,5-trihydro-3,6,9-trioxa-decane chararacterization $^{19}$FNMR in ppm referred to CFCl$_3$=0; –55.7 (3F, CF$_3$O); –63.4 (2F, —ClCF$_2$); –89.5, –91.1 (2F, —OCF$_2$) AB system); –90.8 (4F, —OCF$_2$); –144.7 (1F, —CFH).

$^1$HNMR in ppm referred to TMS=0: 4.4 (2H, CH$_2$); 5.9 (1H, CFH).

Mass spectrum (EI), main peaks and attributions: 363 (M$^+$-Cl); 313 (M-CF$_2$Cl$^+$); 119 (C$_2$F$_5$); 99 (C$_2$H$_2$F$_2$Cl$^+$, 100%), 69 (CF$_3^+$).

IR, main bands (cm$^{-1}$): 2980, 1363, 1209, 1140, 936, 889, 717.

Example 5B

Obtainment of perfluoro-2,5-dihydro-3,6,9-trioxa-1-decene CF$_2$=CH—O—CF$_2$CFHOCF$_2$CF$_2$OCF$_3$ In a glass flask, equipped as described in the preceding Example 1b, but without cold trap, 6.72 g (0.017 moles) of ClCF$_2$—CH$_2$—O—CF$_2$CFHOCF$_2$CF$_2$OCF$_3$ and 0.45 g (0.0009 moles) of tetrabutylammonium hydroxide are introduced. The temperature is brought to 70° C. and under vigorous stirring 1.9 ml of a 50% KOH aqueous solution (equivalent to 1.4 g–0.025 moles) are added drop by drop. The mixture is allowed to react for 30 minutes. At the end water is added to the reaction mixture, the organic phase is separated, it is washed with slightly acid water by HCl and anhydrified. 5.5 g of product are obtained, with a 89.4% yield (product moles/ClCF$_2$—CH$_2$13 O—CF$_2$CFHOCF$_2$CF$_2$OCF$_3$ moles).

Perfluoro-2,5-dihydro-3,6,9-trioxa-1-decene characterization $^{19}$FNMR in ppm referred to CFCl$_3$=0; –55.5 (3F, CF$_3$O); –89.5, –91.1 (2F, —OCF$_2$, AB system); –90.8 (4F, —OCF$_2$); –91.4 (1F, C=CF); –110.2 (1F, C=CF); –144.9 (1F, —CFH).

$^1$HNMR in ppm referred to TMS=0: 6.06 (1H, C=CH); 5.95 (1H, CFHO).

Mass spectrum (EI), main peaks and attributions: 362 (M$^+$); 161 (C$_4$H$_2$F$_5$O$^+$); 119 (C$_2$F$_5^+$, 100%); 101 (C$_2$F$_4^+$) 69 (CF$_3^+$); 51 (CF$_2$H$^+$); 29 (CHO$^+$).

IR, main bands (cm$^{-1}$) 3153, 3105, 3002, 1774, 1364, 1148.

EXAMPLE 6

Perfluoro-2,5-dihydro-3,6,9-trioxa-1-decene
CF$_2$=CH—O—CF$_2$CFHOCF$_2$ CF$_2$OCF$_3$
preparation by reaction of the 2-chloro-2,2-difluoroethyl alcohol with the
CF$_2$=CFOCF$_2$CF$_2$OCF$_3$ compound in tert-butyl alcohol in the presence of soda In a 50 ml volume glass reactor, equipped with PTFE valve and magnetic stirring, 0.8 g (0.007 moles) of 2-chloro-2,2-difluoroethyl alcohol, 2.5 ml of tert-butyl alcohol, 1.5 g (0.027 moles) of KOH and 2.8 g (0.01 moles) of the olefin are introduced. The mixture is left under stirring at room temperature for two hours. At the end the temperature is raised up to 70° C. and it is allowed to react for other two hours. The reaction mixture is diluted with water, the organic phase is recovered, which is washed twice with slightly acid water by HCl, and then ahydrified. 1.5 g of product are obtained. The reaction yield, calculated with reference to the 2-chloro-2,2-difluoroethyl alcohol moles is 60%.

EXAMPLE 7

CF$_2$=CHOCF$_2$CF$_2$H homopolymer

In a 50 ml steel reactor, equipped with magnetic stirring and with inlet for the reactant feeding and discharge, 100 μl of perfluoropropionylperoxide at 6% by weight in CCL$_2$FCF$_2$Cl and 1 g (5.5 mmoles) of CF$_2$=CHOCF$_2$CF$_2$H (Ex. 1) are introduced. The reactor is brought to –196° C. and degassed. After this operation the temperature is raised up to 30° C. and the reaction mixture is kept under stirring for 8 hours. At the end the unreacted monomer is distilled and the polymer is subjected to stripping under vacuum at the temperature of 120° C. for 5 hours. 0.063 g of amorphous homopolymer, having a Tg (DSC) of –9.2° C., are separated.

EXAMPLE 8

CF$_2$=CHOCF$_2$CF$_2$H/TFE 19/81 copolymer (molar ratio)

In a 50 ml steel reactor, equipped with magnetic stirring and inlet for reactant feeding and discharge, cold trap (liq N$_2$), 500 μl of perfluoropropionylperoxide at 6% by weight in CCl$_2$FCF$_2$Cl, 2.8 mmoles of CF$_2$=CHOCF$_2$CF$_2$H (Ex. 1) and 17 mmoles of TFE are introduced. The reactor is heated up to –196° C. and degassed. After this operation the temperature is raised up to 30° C. and the reaction mixture is kept under stirring for 8 hours.

After distillation under vacuum of the solvent and of the unreacted monomers and polymer stripping under vacuum at the temperature of 150° C. for 5 hours, 1.7 g of polymer are separated. The weight balance which is carried out by G.L.C. analysis of the trap content and the $^{19}$FNMR and $^1$HNMR analyses of the polymer dissolved by heating in hexafluorobenzene, allow to determine that the molar percentage of the vinyl ether in the polymer is 19%. The DSC analysis shows a second order transition at the temperature of –56.1° C. The TGA shows a weight loss of 10% at 470° C. The ΔH and the second melting point, determined by DSC, are respectively 8.4 cal/g and 282° C. The polymer is therefore semicrystalline.

EXAMPLE 9

CF$_2$=CHOCF$_2$CF$_2$H/TFE 8/92 copolymer

In a 50 ml steel reactor, equipped with magnetic stirring and inlet for reactant feeding and discharge, cold trap (liq N$_2$), 500 μl of perfluoropropionylperoxide at 6% by weight in CCl$_2$FCF$_2$Cl, 1.8 mmoles of CF$_2$=CHOCF$_2$CF$_2$H (Ext. 1) and 17 mmoles of TFE are introduced.

The reactor is heated up to −196° C. and degassed. After this operation the temperature is raised up to 30° C. and maintained at this temperature until the pressure inside the reactor decreases from 4.2 atm to 2.1 atm. The reaction is stopped by reactor cooling. After distillation under vacuum of the solvent and of the unreacted monomers, and polymer stripping under vacuum at the temperature of 150° C. for 5 hours, 1 g of polymer is isolated. The weight balance, which is carried out by G.L.C. analysis of the trap content, allows to determine that the molar percentage of vinylether present in the polymer is 8%. The DSC analysis shows a second order transition at the temperature of −46° C. The TGA shows a weight loss of 10% at 482° C.

The ΔH and the second melting point, determined by DSC, are respectively 9.9 cal/g and 293.5° C. The polymer is therefore semicrystalline.

EXAMPLE 10

CF$_2$=CH—O—CF$_2$CFHOCF$_2$CF$_2$OCF$_3$/TFE 21/79 amorphous copolymer

In a 50 ml steel reactor, equipped with magnetic stirring and inlet for the reactant feeding and discharge, cold trap (liq N$_2$), 100 μl of perfluoropropionylperoxide at 6% by weight in CCl$_2$FCF$_2$Cl and 1.67 g (4.6 mmoles) of CF$_2$=CH—O—CF$_2$CFHOCF$_2$CF$_2$OCF$_3$ are introduced. The reactor is heated up to −196° C. and degassed. 14 mmoles of TFE are added. The initial internal reactor pressure is 5.1 atm. The mixture is allowed to react for 2.5 hours. The final pressure is of 4.2. The reaction is stopped (20% conversion) bringing the reactor to the liquid nitrogen temperature, connected to a vacuum ramp maintained at the pressure of 10$^{-3}$ mbar. The internal temperature is allowed to rise to the room temperature and the vapours are recovered in a trap cooled at −196° C.

After distillation under vacuum of the solvent and of the unreacted monomers, and polymer stripping under vacuum at the temperature of 150° C. for 5 hours, 604 mg of polymer are separated. The 19FNMR and $^1$HNMR analysis of the polymer dissolved in hexafluorobenzene allows to determine that the ether molar percentage is 21%. The polymer is amorphous and shows a Tg, determined by DSC, at −24.7° C. The TGA shows a weight loss of 10% at 473° C.

EXAMPLE 11

CF$_2$=CFOCF$_2$CF$_2$CF$_3$/CF$_2$=CHOCF$_2$CF$_2$H/TFE 12/13/75 amorphous terpolymer In a 50 ml steel reactor, equipped with magnetic stirring and inlet for the reactant feeding and discharge, 100 μl of perfluoropropionylperoxide at 6% by weight in CCl$_2$FCF$_2$Cl, 1 ml of TFE and 0.9 g (5 mmoles) of CF$_2$=CHOCF$_2$CF$_2$H (Ex. 1) and 1.33 g (5 mmoles) of CF$_2$=CFOCF$_2$CF$_2$CF$_3$ are introduced. The reactor is heated up to −196° C. and degassed. 9 mmoles of TFE are added and the temperature is raised up to 40° C. The mixture is allowed to react and the reactor internal pressure is let to lower from 5.1 atm to 3.13 atm. The reaction is stopped (48% conversion) and the reactor is cooled to the liquid nitrogen temperature, connected to a vacuum ramp maintained at the pressure of 10$^{-3}$ mbar. The reactor internal temperature is allowed to rise to the room temperature and the vapours are recovered in a trap cooled at −196° C.

After distillation under vacuum of the solvent and of the unreacted monomers, and polymer stripping under vacuum at the temperature of 150° C. for 5 hours, 645 mg of polymer are recovered. The polymer molar composition is determined by $^{19}$FNMR and $^1$HNMR analysis dissolving the substance in hexafluorobenzene.

The molar composition results to be the following: CF$_2$=CFOCF$_2$CF$_2$CF$_3$ 12%, CF$_2$=CHOCF$_2$CF$_2$H 13%, TFE 75%. The polymer is amorphous and shows a Tg at 8° C. (determined by DSC). The TGA shows a weight loss of 10% at 452> C.

EXAMPLE 12

Perfluoro-2,5-dihydro3,6,9,11,13,15,17-heptaoxa-octadecan-1-ene CF$_2$=CH—O—CF$_2$CFHOCF$_2$CF$_2$O(CF$_2$O)$_4$CF$_3$ preparation

Example 12A

Perfluoro-1-chloro-2,2,5-trihydro-3,6,9,11,13,15,17-heptaoxa-octadecane preparation ClCF$_2$CH$_2$—O—CF$_2$CFHOCF$_2$CF$_2$O(CF$_2$O)$_4$CF$_3$ The method described in Example 2A is followed. 10.8 g (0.103 moles) of ClCF$_2$CH$_2$OH, 30 ml of terbutylic alcohol, 4 g (0.07 moles) of KOH and 40 g (0.07 moles) of CF$_2$=CFOCF$_2$CF$_2$O(CF$_2$O)$_4$CF$_3$ obtained according to U.S. Pat. No. 3,817,960 are used.

At the end 37 g of the compound with a yield 80% are obtained.

Perfluoro-1-chloro-2,2,5-trihydro-3,6,9,11,13,15,17-heptaoxa-octadecane characterization $^{19}$FNMR in ppm referred to CFCl$_3$=0; −55.6 (3F, OCF$_3$); from −53 to −57 (8F, —OCF$_2$Cl); −63.3 (2F, —CF$_2$Cl); from −85 to −90 (6F, CF$_2$O); −144.5 (1F, —CFH).

$^1$HNMR in ppm referred to TMS=0: 4.3 (2H, CH$_2$); 5.9 (1H, CFH).

IR, main bands (cm$^{-1}$): 2978, da 1400 a 1050, 730, 692, 547

Example 12B

Obtainment of perfluoro-2,5-dihydro-3,6,9,11,13,15,17-heptaoxa-octedecan-1-ene CF$_2$=CH—O—CF$_2$CFHOCF$_2$CF$_2$O)$_4$CF$_3$ In a 250 ml three-necked glass flask, equipped with magnetic stirrer, thermometer and dropping funnel, 47.2 g (0.075 moles) of the compound obtained in Ex. 12A and 4 g (0.015 moles) of tetrabutylammonium hydroxide are introduced. To the mixture 10 g (0.18 moles) of solid KOH are added. The mixture is then heated up to 50° C. and let react for 3 hours. It is cooled at room temperature and slightly acid water by HCl is added. The organic phase is separated and dried. The mass is distilled obtaining 42 g of the product with a yield 93%.

Perfluoro-2,5-dihydro-3,6,9,11,13,15,17-heptaoxa-octedecan-1-ene characterization $^{19}$FNMR in ppm referred to CFCl$_3$=0; −54.4 (2F, OCF$_2$O); −56.1 (4F, OCF$_2$O); −56.8 (2F, OCF$_2$O); −58.8

(3F, CF$_3$); −90.8 (2F, CF$_2$); −91.8 (2F, CF$_2$); −90.4, −92.0 (2F, —CF$_2$, AB system); −92,2 (1F, C=CF$_2$); −108.7 (1F, C=CF$_2$); −142.5 (1F, —CFH).

1HNMR in ppm referred to TMS=0: 6.04 (1H, C=CH); 5.94 (1H, CFHO).

IR, main bands (cm$^{-1}$): 3152, 3106, 3002, 1774, 1350–1050, 730, 693.

EXAMPLE 13

Perfluoro-4-hydro-4-methoxy-5-(1-hydro-vinyloxy)-1,3-dioxolane preparation

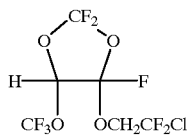

Example 13A

Perfluoro-4-hydro-4-methoxy-5-(2-chloro-1,1-dihydroethoxy)-1,3-dioxolane preparation The product is obtained according to the method described in Example 2A, using 5.5 g (0.048 moles) of ClCF$_2$CH$_2$OH, 15 ml of terbutylic alcohol, 27 g (0.048 moles) of KOH and 10 g (0.048 moles) of perfluoro-4-methoxy-1,3-dioxole, obtained according to EP 633,257. 14 g of product with yield 91% are obtained.

Perfluoro-4-hydro-4-methoxy-5-(2-chloro-1,1-dihydroethoxyl-1,3-dioxolane characterization 19FNMR in ppm referred to CFCl$_3$=0; isomer sin: −53.7, −58 (2F, —OCF$_2$O, AB system); −59.8 (3F, OCF$_3$); −63.6 (2F, CF$_2$Cl); −77.9 (1F, CF). isomer anti: −52.7, −58.1 (2F, —OCF$_2$O, AB system); −59.9 (3F, OCF$_3$); −63.4 (2F, CF$_2$Cl); −78.7 (1F, CF).

$^1$HNMR in ppm referred to TMS=0: isomer sin: 4.4 (2H, CH$_2$); 5.88 (1H, CH) isomer anti: 4.35 (2H, CH$_2$); 5.86 (1H, CH).

Mass spectrum (EI), main peaks and attributions: 241 (M$^+$-CF$_2$Cl)

IR, main bands (cm$^{-1}$): 3030, 2975, 1422, 1360, 1320, 1198, 1051, 982, 892, 754, 677.

Example 13B

Obtainment of perfluoro-4-hydro-4-methoxy-5-(1-hydro-vinyloxy)-1,3-dioxolane

In a 100 ml three-necked glass flask equipped with magnetic stirrer, thermometer, dropping funnel and reflux 13.2 g (0.031 moles) of the compound obtained in Ex 13A, 55 g of a 40% by weight K$_2$CO$_3$ aqueous solution (equivalent to 22 g–0.065 moles of carbonate) and 2 g (0.008 moles) of tetrabutylammonium hydroxide are fed. The mixture is allowed to react at 60° C. for 5 hours under vigorous stirring. It is cooled and slightly acid water by HCl is added. The organic phase is separated and dried. 8.6 g of product with yield 95% are obtained.

Perfluoro-4-hydro-4-methoxy-5- 1-hydro-vinyloxy)-1,3-dioxolane characterization $^{19}$FNMR in ppm referred to CFCl$_3$=0; isomer sin: −53.6, −58.1 (2F, —OCF$_2$O, AB system); −59.78 (3F, CF$_3$); −78.6 (1F, CF); −91.8 (1F, C=CF$_2$); −110.7 (1F, C=CF$_2$) isomer anti: −52.8, −58.2 (2F, —OCF$_2$O, AB system); −59.82 (3F, CF$_3$); −92,2 (1F, C=CF$_2$); −94.2 (1F, CF); −109.8 (1F, C=CF$_2$).

$^1$HNMR in ppm referred to TMS=0: isomer sin: 5.9 (1H, CH); 6.08 (1H, C=CH). isomer anti: 5.8 (1H, CH); 6.04 (1H, C=CH).

Mass spectrum (EI), main peaks and attributions: 290 (M$^+$); 224 (M$^+$-COF$_2$) 145 (C$_3$HF$_4$O$_2^+$); 69 (CF$_3^+$, 100%); 29 (CHO$^+$).

IR, main bands (cm$^{-1}$): 3153, 3104, 3031, 1774, 1360, 1320, 1198, 1051, 936, 892, 790, 754, 677, 621, 543.

EXAMPLE 14

Amorphous copolymer CF$_2$=CH—O—CF$_2$CFHOCF$_3$ and TFE 20/80

In a 50 ml steel reactor, equipped with magnetic stirring and inlet for the reactant feeding and discharge, with a cold trap (liq N$_2$) 100 µl of perfluoropropionylperoxide at 6% by weight in CCl$_2$FCF$_2$Cl, 0.98 g (4 mmoles) of CF$_2$=CH—O—CF$_2$CFHOCF$_3$ (Ex. 4) are introduced. The reactor is heated up to −196° C. and degassed. 12 mmoles of TFE are fed and the reactor inside is heated up to 30° C. The reaction is stopped after 5 hours by lowering the temperature to that of the liquid nitrogen, with the reactor connected to a vacuum ramp maintained at the pressure of 10$^{-3}$ mbar. It is then let reach room temperature, recovering the vapours in the trap cooled at −196° C.

After distillation of the solvent and of the unreacted monomers and polymer stripping under vacuum at 150° C. for 5 hours, 432 mg of polymer are isolated. The weight balance determined by G.L.C. of the traps containing the unreacted monomers allows to determine that the molar percentage of the vinylether in the polymer is of 20%. The obtained polymer is amorphous and shows a Tg, determined by DSC, at −6.4° C. The TGA shows a weight loss of 10% at 469° C.

EXAMPLE 15

Amorphous copolymer perfluoro-4-hydro-4-methoxy-5-(1-hydro-vinyloxy)-1,3-dioxolane and TFE 10/20

In a 50 ml steel reactor, equipped with magnetic stirring and inlet for the reactant feeding and discharge, with cold trap (liq N$_2$) 200 µl of perfluoropropionylperoxide at 6% by weight in CCl$_2$FCF$_2$Cl, 1.45 g (5 mmoles) of perfluoro-4-hydro-4-methoxy-5-(1-hydro-vinyloxy)-1,3-dioxolane (Ex. 13) are introduced. The reactor is heated up to −196° and degassed. TFE (12 mmoles) is added and the inside of the reactor is heated up to a temperature of 35° C. The reaction is stopped after 5 hours (60% TFE conversion), cooling the reactor to the liquid nitrogen temperature, connected to a vacuum ramp maintained at the pressure of 10$^{-3}$ mbar. It is then let reach room temperature recovering the vapours in the trap cooled at −196° C.

After distillation of the solvent and of the unreacted monomers and polymer stripping under vacuum at 150° C. for 5 hours, 981 g of polymer are isolated. By the weight balance, carried out by G.L.C., it is determined that the molar percentage of vinylether in the polymer is of 10%. The polymer is amorphous and shows a Tg, determined by DSC at 7.3° C. The TGA shows a weight loss of 10% at 448° C.

EXAMPLE 16

CF$_2$=CH—O—CF$_2$CFHOCF$_2$CF$_2$O(CF$_2$O)$_4$CF$_3$/ TFE 15/85 copolymer

In a 50 ml steel reactor, equipped with magnetic stirring and inlet for the reactant feeding and discharge, with cold trap (liq $N_2$) 200 μl of perfluoropropionylperoxide at 6% by weight in $CCl_2FCF_2Cl$ are introduced, feeding 1.56 g (2.5 mmoles) of $CF_2$=CH—O—$CF_2CFHOCF_2CF_2O$ $(CF_2O)_4$ $CF_3$ (Ex. 12). TFE (12 mmoles) are added and the temperature inside the reactor is increased up to 35° C. The reaction is stopped when the TFE conversion is 70% cooling the reactor to the liquid nitrogen temperature, connected to a vacuum ramp maintained at the pressure of $10^{-3}$ mbar. It is then let reach room temperature recovering the vapours in the trap cooled at –196° C.

The solvent and the unreacted monomers are distilled, and then the polymer stripping under vacuum at 150° C. for 5 hours is carried out.

From the weight balance determined by G.L.C. on the basis of the trap unreacted monomer content, it results that the vinylether percentage in the polymer is of 15%. The obtained polymer is amorphous and shows a Tg, determined by DSC, at –80° C.

EXAMPLE 17

TFE 28/72 copolymer

In a 50 ml reactor, equipped with magnetic stirring and inlet for the reactant feeding and discharge, with cold trap (liq $N_2$), 200 μl of perfluoropropionylperoxide at 6% by weight in $CCl_2FCF_2Cl$, 3.13 g (5 mmoles) of $CF_2$=CH—O—C—$F_2CFHOCF_2CF_2O(CF_2O)_4CF_3$ (Ex. 12) are introduced. The reactor is cooled to –196° C. and degassed. TFE (12 mmoles) is added and the temperature inside the reactor is increased up to 35° C. The reaction is stopped when the TFE conversion is 65%, cooling the reactor to the liquid nitrogen temperature, connected to a vacuum ramp maintained at the pressure of $10^{-3}$ mbar. It is then let reach room temperature recovering the vapours in the trap cooled at –196° C.

After distillation of the solvent and of the unreacted monomers and polymer stripping under vacuum at 150° C. for 5 hours, from the weight balance determined by G.L.C., on the basis of the trap unreacted monomer content, it results that the vinylether percentage in the polymer is 28%.

Example 18 (Comparative)

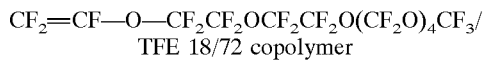
TFE 18/72 copolymer

By repeating Example 17, but using instead of $CF_2$=CH—O—$CF_2CFHOCF_2OCF_2CF_2O_4CF_3$ the $CF_2$=CF—O—$CF_2CF_2OCF_2O(CF_2CF_2O_4CF_3$ perfluorovinylether, obtained according to U.S. Pat. No. 3,817,960, in the same molar amounts, it results that the perfluorovinylether percentage in the polymer is 18%. The polymer is amorphous and shows a Tg, determined by DSC, at –72.5° C.

TABLE 1

| Copolymers TFE/ethers | polymer | | Temperature |
|---|---|---|---|
| | % molar vinylether | % by weight H | 10% weight loss (° C.) |
| Invention examples | | | |
| 8 | 19[(1)] | 0.3 | 470 |
| 9 | 8[(1)] | 0.2 | 482 |
| 10 | 21[(2)] | 0.3 | 473 |

TABLE 1-continued

| Copolymers TFE/ethers | polymer | | Temperature |
|---|---|---|---|
| | % molar vinylether | % by weight H | 10% weight loss (° C.) |
| 14 | 20[(3)] | 0.3 | 469 |
| 15 | 21[(4)] | 0.3 | 448 |
| Examples of EP-A-338755 (ref. Table 3) | | | |
| 3* | 5.8 | 0.1 | 380** |
| 3[F] | | | 440** |
| 4* | 12 | 0.2 | 350** |
| 4[F] | | | 420** |
| 5* | 25 | 0.3 | 330** |
| 5[F] | | | 410** |

[(1)]vinylether: $CF_2$=CHOCF$_2$CF$_2$H
[(2)]vinylether: $CF_2$=CH—O—CF$_2$CFHOCF$_2$CF$_2$OCF$_3$
[(3)]vinylether: $CF_2$=CH—O—CF$_2$CFHOCF$_3$
[(4)]vinylether: perfluoro-4-hydro-4-methoxy-5-(1-hydro-vinyloxy)-1,3-dioxolane
*Non fluorinated copolymer TFE/$CF_2$=CFOCH$_2$CF$_2$CF$_3$ ref. Table 3 of EP-A-338755
[F]copolymer TFE/$CF_2$=CFOCH$_2$CF$_2$CF$_3$ fluorinated with elemtal fluorine, ref. Table 3 EP-A-338755
**Decomposition temperatures, ref. Table 3 of EP-A-338755

What is claimed is:

1. Vinylethers having the formula:

$$CF_2=CH-O-R_A \qquad (I)$$

wherein $R_A$ is a radical containing fluorine and hydrogen, optionally containing halogen atoms selected from the group consisting of Cl and Br; and $R_A$ is selected from the group consisting of:

linear or branched, saturated or unsaturated $C_2$–$C_{20}$ fluoroalkyl group;

saturated or unsaturated $C_4$–$C_6$ fluorinated cyclic group; wherein optionally from 1 to 2 carbon atoms are substituted with oxygen atoms forming ethereal bonds;

linear, branched, saturated or unsaturated $C_3$–$C_{15}$ fluorooxyalkyl group, containing one or more oxygen atoms forming ethereal bonds.

2. Vinylethers according to claim 1 wherein the $R_A$ radical has the following meanings:

$CF_2$—$R_C$
    wherein $R_C$ is selected from the following:
        a linear or branched, saturated or unsaturated $C_1$–$C_{19}$ fluoroalkyl group;
        a linear or branched, saturated or unsaturated $C_2$–$C_{14}$ fluorooxyalkyl group, containing one or more oxygen atoms forming ethereal bonds;

$CF_2$—CFH—$R_D$
    wherein $R_D$ is selected from the following:
        a linear or branched, saturated or unsaturated $C_1$–$C_{18}$ perfluoroalkyl group;
        a linear or branched, saturated or unsaturated $C_1$–$Cl_{13}$ perfluorooxyalkyl group, containing one or more oxygen atoms forming ethereal bonds.

3. Vinylethers according to claim 1 wherein the $R_A$ radical contains functional groups selected from CN, COOR', CON(R')$_2$, SO$_2$OR', wherein R' is a linear or branched $C_1$–$C_5$ alkyl group.

4. Polymers and copolymers obtainable by copolymerizing with the hydro-fluoroalkylvinylethers of claim 1 totally or partially fluorinated and non fluorinated comonomers having at least one unsaturation of ethylenic type.

5. Copolymers according to claim 4 wherein the comonomers are the following:
C$_2$–C$_8$ perfluoroolefins;
hydrogenated C$_2$–C$_8$ fluoroolefins;
chloro- and/or bromo- and/or iodo C$_2$–C$_8$ fluoroolefins.
(per)fluoroalkylvinylethers (PAVE) CF$_2$=CFOR$_f$, wherein R$_f$ is a C$_1$–C$_6$ (per)fluoroalkyl group;
CF$_2$=CFOX" (per)fluoro-oxyalkylvinylethers, wherein X" is C$_1$–C$_{12}$ alkyl, or C$_1$–C$_{12}$ oxyalkyl, or C$_1$–C$_{12}$ (per)fluorooxyalkyl having one or more ethereal groups;
perfluorodioxole (PD), perfluoro (2,2-dimethyl)-1,3-dioxole (PDD), perfluoro-4-methoxy-1,3-dioxole (TTD);
CF$_2$=CF—O—CF$_2$—O—CF=CF$_2$ (bis-vinyloxymethane, EVOM);
CF$_2$=CF—O—CF$_2$—CF$_2$—SO$_2$F.

6. Copolymers according to claim 4, wherein the comonomer is tetrafluoroethylene.

7. A process for obtaining the hydrofluoroalkylvinylethers of claim 1, wherein one of the reactants is a 2-Hal-2,2-difluoroethylic alcohol, wherein Hal=Cl, Br, comprising the following steps:

A) obtainment of a 2-Hal-2,2-difluoroethyl fluoroalkyl ether by reaction of the 2-Hal-2,2-difluoroethylic alcohol in the presence of an alkaline or earth-alkaline metal hydroxide, in molar ratio with respect to the alcohol in the range 0.2–1, with an unsaturated compound selected from the following:

A1) an unsaturated fluoroalkyl compound having the formula $$XFC=CYZ \qquad (II)$$

according to the following scheme:

$$Hal\text{—}CF_3\text{—}CH_2OH + XFC=CYZ \xrightarrow{OH^-}$$
$$Hal\text{—}CF_2\text{—}CH_2O\text{—}CFX\text{—}CYZH$$

(IIa)

wherein:
the total number of carbon atoms of —CFX—CYZH is as defined for R$_A$;
X=F, R'f$_X$, OR'f$_X$,
Y=F, H, Cl, Br, I, R'f$_Y$, OR'f$_Y$;
Z=F, H, Cl, Br, I, R'f$_Z$, OR'f$_Z$;
when one or more fluorooxyalkyl groups are present the total number of oxygen atoms is equal to that of R$_A$;
R'f$_X$, R'f$_Y$, R'f$_Z$, equal to or different from each other, are fluorinated alkyl groups which optionally contain one or more oxygen atoms forming ethereral bonds and/or one or more halogen atoms such as Cl, Br, I; R'If R'f$_Y$, R'f$_Z$ can optionally contain one or more functional groups, stable in the reaction conditions, such as CN, COOR', CON(R')$_2$ wherein R' is as above defined;

A2) A perfluorinated C$_4$–C$_6$ cyclic compound containing a double bond, in which optionally from 1 to 2 carbon atoms can be substituted with oxygen atoms (compound III); when no oxygen is directly bound to the unsaturation, the reaction scheme is the following:

$$HalCF_2CH_2OH + \underset{(III a)}{\underset{F\quad F}{\bigcirc^{(CF_2)_n}}} \xrightarrow[F^-]{OH^-} \underset{HalCF_2CH_2O\quad F}{\bigcirc^{(CF_2)_n}}$$

wherein n is an integer comprised between 2 and 4; otherwise the reaction takes place as in A1) and a saturated compound is obtained;

A3) a disubstituted perfluoroalkyne having the formula:

$$R"f\text{—}C\equiv C\text{—}R'''f \qquad (IV)$$

according to the following scheme:

$$Hal\text{—}CF_2\text{—}CH_2OH + R"f\text{—}C\equiv C\text{—}R'''f \xrightarrow{OH^-}$$
$$Hal\text{—}CF_2\text{—}CH_2O\text{—}C(R"f)=C(R'''f)H$$

(IVa)

wherein:
R"f and R'''f are F or C$_1$–C$_2$ perfluoroalkyl, with the proviso that R"f and R'''f are not contemporaneously F;
in organic solvent at a temperature in the range 0° C.–50° C; diluting at the end of the reaction with acidulated water, separating the organic phase and recovering the product;

B) dehydrohalogenation of the fluoroalkyl Hal-difluoroethylethers in the presence of organic or inorganic bases, in aqueous or organic solvent or respective mixtures, and recovery of the final product.

8. A process according to claim 7 wherein in step A) the hydroxide is alkaline metal and the temperature is in the range 10° C.–40° C.

9. A process according to claim 7 wherein in step B) dehydrohalogenation is carried out under phase transfer conditions, using as phase transfer agent a phosphonium salt or a quaternary ammonium salt, the alkali is aqueous and has a concentration in the range 20%–60% w/w, the temperature is in the range 20° C.–100° C.

10. A process according to claim 7, wherein the 2-Hal-2,2-di-fluoroethylic alcohol, wherein Hal has the meaning indicated in claim 7, is let react at a temperature in the range 50°–80° C. with one of the unsaturated compounds (I-I), (III), (IV) of A), using as solvent the tert-butylic alcohol, in the presence of an alkaline or earth-alkaline metal hydroxide in a molar ratio with the 2-Hal-2,2-difluoroethylic alcohol comprised between 2 and 5.

* * * * *